United States Patent [19]
Tomasso et al.

[11] Patent Number: 5,518,693
[45] Date of Patent: May 21, 1996

[54] TRANSFER MECHANISM FOR AUTOMATIC LOADING AND UNLOADING OF REAGENT MODULES

[75] Inventors: David A. Tomasso, Rochester; Johannes J. Porte, Webster, both of N.Y.

[73] Assignee: Johnson & Johnson Clinical Diagnostics, Inc., Rochester, N.Y.

[21] Appl. No.: 267,086

[22] Filed: Jun. 27, 1994

[51] Int. Cl.⁶ .................................................. G01N 35/04
[52] U.S. Cl. .............................. 422/63; 422/64; 422/65; 436/43; 436/47; 436/48
[58] Field of Search ................................ 422/63, 64, 65, 422/100; 436/43, 47, 48, 180

[56] References Cited

U.S. PATENT DOCUMENTS

| | | | |
|---|---|---|---|
| 3,985,507 | 10/1976 | Litz et al. | 23/253 R |
| 4,678,752 | 7/1987 | Thorne et al. | 435/291 |
| 5,055,262 | 10/1991 | Sakagami | 422/64 |
| 5,066,135 | 11/1991 | Meyer et al. | 366/208 |
| 5,075,082 | 12/1991 | Fechtner | 422/102 |
| 5,219,526 | 6/1993 | Long | 422/64 |
| 5,320,808 | 6/1994 | Holen et al. | 422/64 |
| 5,332,549 | 7/1994 | MacIndoe, Jr. | 422/63 |
| 5,358,691 | 10/1994 | Clark et al. | 422/64 |

*Primary Examiner*—Jill Warden
*Assistant Examiner*—Long V. Le
*Attorney, Agent, or Firm*—Dana M. Schmidt

[57] ABSTRACT

Apparatus and a method for automatically transferring by pushing and pulling a reagent module onto and off of a rotor of modules. A surface of the module and the transfer mechanism are cooperatively shaped with a loose-fitting tongue and arcuate groove, both the tongue and groove having a curved extension along an arc concentric with the axis of rotation of the rotor, such that modules mounted on the rotor can be rotated off the transfer mechanism by sliding the tongue relative to the groove in a rotational direction. An additional groove is provided at an angle to said arcuate groove, along which the tongue or arcuate groove, whichever is on the transfer mechanism, reciprocates to push or pull a module into or out of the rotor.

6 Claims, 7 Drawing Sheets

TRANSFER MECHANISM FOR AUTOMATIC LOADING AND UNLOADING OF REAGENT MODULES

FIELD OF THE INVENTION

This invention relates to apparatus for a method of automatically loading and unloading reagent modules into and off of a rotor, from a load station, such as is used in a wet assay chemical analyzer.

BACKGROUND OF THE INVENTION

It is known in wet assay analyzers to provide cartridges of reagents to a rotor, by inserting them along a radius of the rotor where they are processed with the other cartridges likewise inserted. Examples, are shown in, e.g., U.S. Pat. Nos. 5,075,082 and 5,219,526. However, previous constructions have either required the insertion into the rotor to be manual, as in the '082 patent, or to be done by using a pusher that has to be withdrawn afterwards before the rotor can rotate, the pusher being effective only to load a cartridge, and not to unload it, as shown in the '526 patent.

Therefore, prior to this invention there has been a need for automated means for insertion of reagent cartridges into a rotor that is versatile enough to both a) remain inside the rotor enclosure during rotor rotation and b) act to withdraw a spent cartridge as well as insert a new one.

RELATED APPLICATION

Commonly owned U.S. application Ser. No. 086,408 filed on Jul. 1, 1993 by D. Tomasso entitled "Locked Bottle Holder" (Docket 66138A), now U.S. Pat. No. 5,322,668, discloses, but it does not claim, the grooves of the undersurface of the reagent module. No transfer mechanism is disclosed, since that application is directed to structures for locking the module together.

SUMMARY OF THE INVENTION

We have devised an analyzer transfer mechanism for reagent cartridges which solves the above-noted problems.

More specifically, in accordance with one aspect of the invention, there is provided an analyzer comprising a source of reagents and reaction cuvettes, the analyzer including a rotor,having a periphery and an axis of rotation, a drive for rotating the rotor about the axis, the source comprising a removable module containing a reagent container and a stack of cuvettes, the rotor including receiving stations constructed to receive and engage the modules, a load and unload station for receiving and returning individual modules from and to an operator, and transfer means for transferring an individual module on the load station in a first direction onto the rotor. The analyzer is improved in that the transfer means and the modules comprise between them, a member with a projecting tongue on one of the transfer means and the modules, and a cooperatively shaped groove on the other of the transfer means and the modules for reception of the tongue within it, the groove being dimensioned to freely slideably accommodate the tongue within it, said tongue and groove having an extension in a direction that is misaligned with the first direction, so that the tongue and groove are effective to move an engaged module onto or off of the rotor along the first direction.

In accord with another aspect of the invention, there is provided a method of moving a reagent module into and out of a rotor having an enclosure and a drive axis in an analyzer using a transfer member with a projecting tongue and modules with a mating groove, the method comprising:

a) loading a first module onto a load platform outside of the rotor so that the groove is fitted over the tongue, b) pushing the tongue against the groove in a direction that enters the rotor enclosure with the module passing onto the rotor, c) rotating the rotor and the module while the tongue is inside the enclosure so that the tongue slides out of the groove and into a corresponding groove of another module on the rotor that is substantially identical to the first module, and d) when a module is ready to be withdrawn, pulling the ready module off of the rotor by pulling a tongue of a transfer member against the groove of the module in a direction out of the rotor enclosure.

Thus it is an advantageous feature of the invention that reagent cartridges or modules (hereinafter, "modules") are loaded and unloaded from the rotor automatically by a transfer mechanism that can remain inside the rotor enclosure while the rotor is rotating to index or move along the modules.

It is a related advantageous feature of the invention that a single transfer mechanism can be used to accomplish both the loading and unloading of said modules.

Other advantageous features will become apparent upon reference to the following "Detailed Description" when read in light of the attached drawings.

DESCRIPTION OF THE PREFERRED EMBODIMENTS

The following description is presented in the context of the preferred embodiments, in which a reagent module is loaded and unloaded into and out of a rotor therefor along a radius of the rotor, using a particular shape and contents for the module, for use in a preferred wet assay analyzer. In addition, it is useful regardless of the direction of loading and unloading of the modules, the shape and contents of the modules, or the rest of the analyzer's construction, provided that the module provides the interaction with the transfer mechanism that is the primary feature of the invention.

Figure 1:
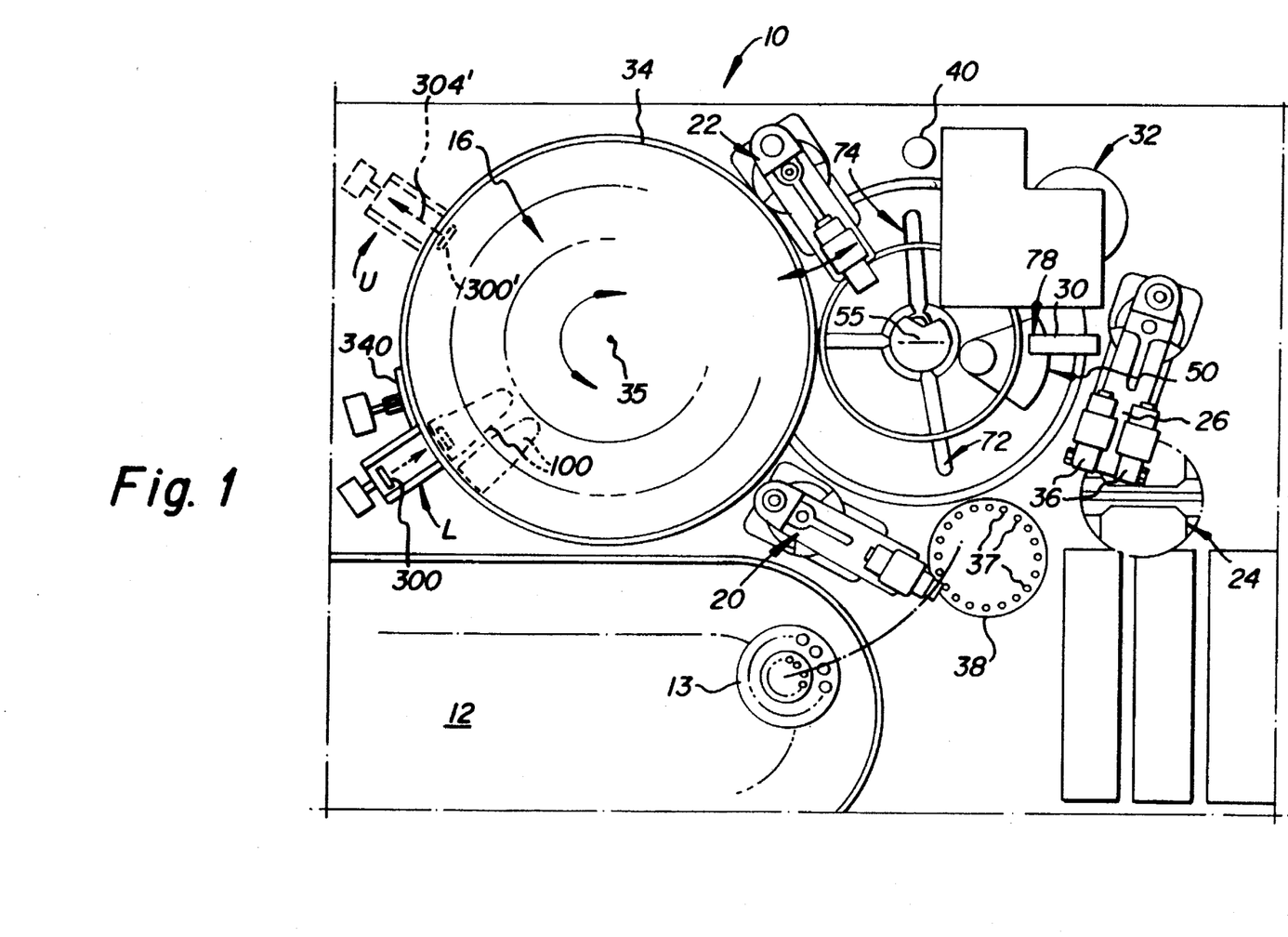
FIG. 1 is a fragmentary plan view of an analyzer in which the rotor and module transfer means of the invention is useful.
Figure 2:
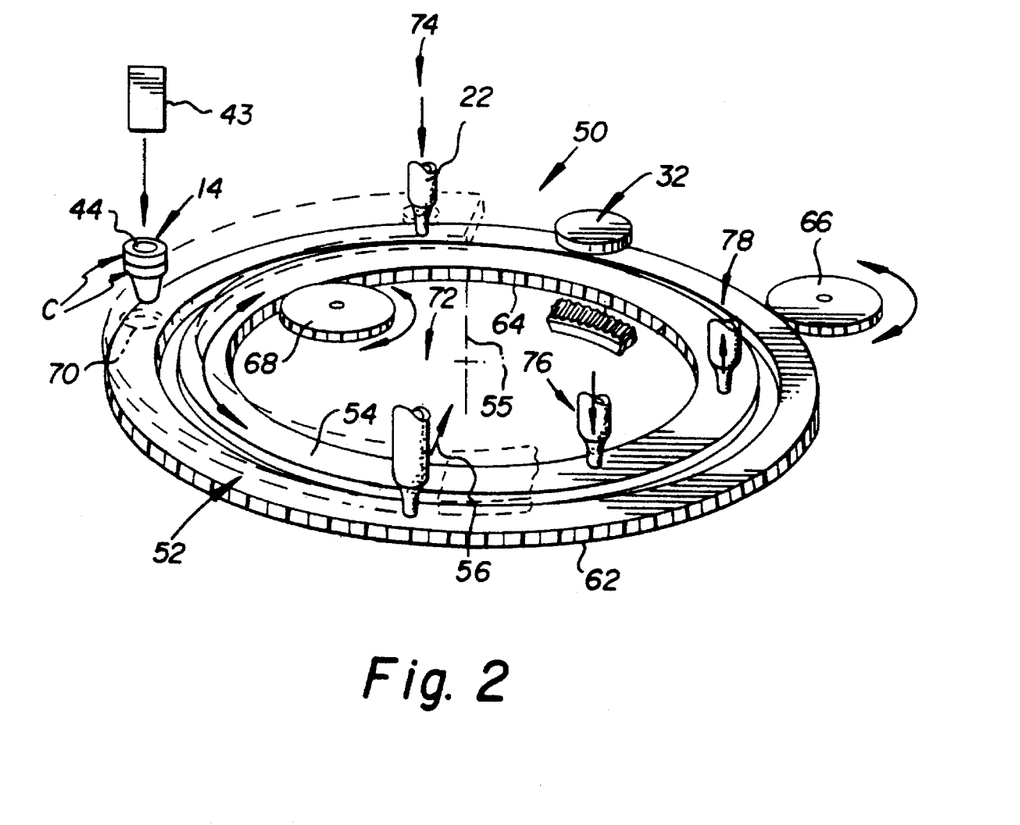
FIG. 2 is a partially schematic, isometric view of two rotors of an incubator of the analyzer, showing the various stations.

As shown in FIG. 1, an analyzer 10 in which the reagent modules and their rotor are used, preferably comprises sample supply station 12, a cuvette supply station 14, FIG. 2, a reagent supply station 16, FIG. 1, incubator 50, means 20 and 22 for transferring sample and reagent to a cuvette disposed in an outer ring of incubator 50, signal reagent supply station 24, means 26 for transferring signal reagent to the cuvette in an inner ring of incubator 50, cuvette wash station 30, and luminometer 32, all as described in commonly-owned U.S. Pat. No. 5,244,633. Any suitable construction can be used for the sample supply station 12, cuvette supply station 14, reagent supply station 16, transfer means 20, 22 and 26, signal reagent supply station 24, wash dispenser 30, and luminometer 32. Useful sample transfer devices 13 include those described and claimed in commonly owned, U.S. application Ser. No. 859,780 filed on Mar. 30, 1992 by Tomasso et al, entitled "Tray and Magnetic Conveyor", now abandoned in favor of U.S. continuation-in-part application Ser. No. 036,800, filed Mar. 25, 1993 now U.S. Pat. No. 5,366,697. Supply station 16 includes a rotor 34 having an axis of rotation 35. Transfer means 20, 22 and 26 are all preferably pivoting aspirators, the aspirator at transfer means 26 having dual probes 36. Transfer means 20 preferably uses disposable tips, which can be presented for pick-up on supply station 12. Additional tips 37 can be presented on turntable 38 for use by means 20 during a dilution step. On the other hand, the aspirator for transfer means 22 preferably uses a more permanent dispensing tip, which uses a wash station 40 as is conventional.

Cuvettes are provided for dispensing at station 14 by mounting them, preferably, in the reagent module 100 discussed below, shown in phantom FIG. 1.

Although any cuvette can be used, preferably it is a cup-like container "C", having on its inside wall surface 44 an antibody pre-attached to the wall surface, FIG. 2. The antibody is useful in a conventional sandwich assay which produces a complex of antibody-antigen labeled antibody for generating a chemiluminescent signal.

The incubator is preferably that disclosed in said '633 patent, and comprises two rotors which are preferably two concentrically mounted support rings 52, 54 provided with holding apertures (not shown) for receiving and carrying cuvettes C (delivered preferably first to ring 52 by any pusher means 43, FIG. 2), rotating means for independently rotating rings 52 and 54 about a common axis 55, transfer means (not shown) for moving a cuvette, arrow 56 of FIG. 2, from ring 52 to 54, and then off ring 54, processing stations around the rings, and heating means to incubate the contents of the cuvettes on rings 52 and 54. Rings 52 and 54 are shown only schematically in FIG. 2 in association with the related components. Rotating means for the rings preferably comprise gear teeth 62, 64 disposed on each of rings 52 and 54, respectively, to be driven by pinion gears 66 and 68.

As noted above, various processing stations are disposed around the circumference of rings 52 and 54, in addition to an entrance port 70 for cuvettes C. They are as follows, FIGS. 1 and 2: Station 72 is permanently disposed above ring 52 and is the place to which the dispensing tip 37 of aspirator 20, FIG. 1, pivots and descends to dispense sample into a cuvette in ring 52, FIG. 2. First reagent addition station 74 is permanently disposed at least above ring 52 so that the permanent tip of aspirator 22 can dispense at least a first reagent into a cuvette in ring 52. Optionally, aspirator 22 can also be used to dispense a second reagent, namely a conjugate reagent, as well. A further reagent addition station 76, here for signal reagent, is disposed permanently above at least inner ring 54, to descend to dispense signal reagent into a cuvette in ring 54. Wash dispensing station 78 is disposed permanently above ring 54 for washing cuvettes using wash dispenser 30. Luminometer 32 is permanently disposed above ring 54 for reading chemiluminescence.

Final removal of the used, finished cuvette from ring 54 can be achieved by any suitable mechanism.

Figure 3:
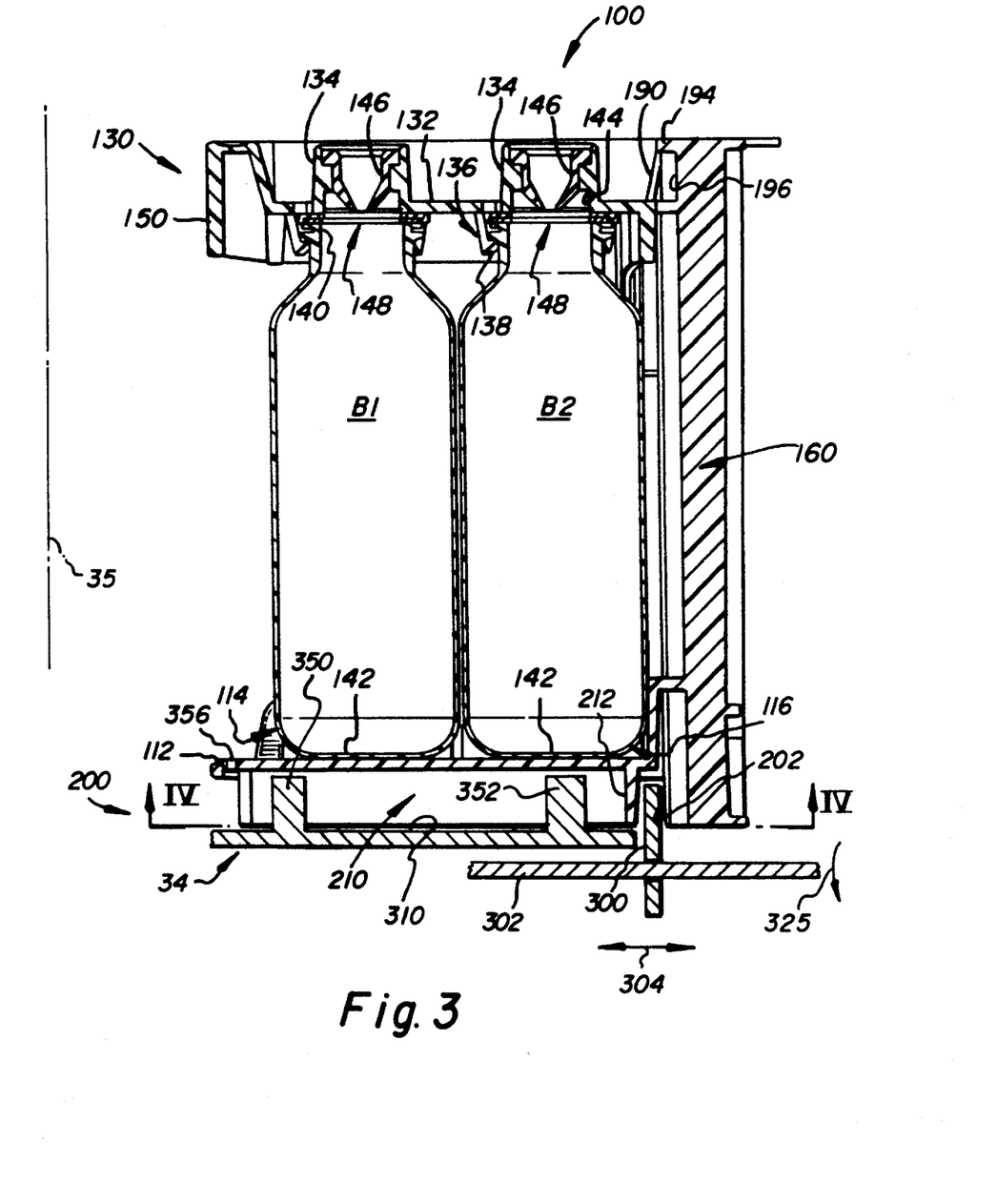
FIG. 3 is a fragmentary elevational view in section of the reagent module and transfer mechanism for the module, shown inside the enclosure of the rotor of modules.

The reagent module 100, FIG. 3, is preferably of the type described in commonly owned U.S. application Ser. No. 086,408 (Docket 66138A) filed in Jul. 1, 1993 by D. Tomasso et al entitled "Locked Bottle Holder", now U.S. Pat. No. 5,322,688. More specifically, module 100 is generally pie-shaped, FIG. 4, so as to slide in and out of rotor 34 generally in a circular arrangement of such holders, FIG. 1. Such a module 100 comprises a base 112, FIG. 3, a top member 130, and a sidewall 160 extending between and joined to the base and top member.

Base 112 comprises in turn a platform having at least one recess and preferably recesses 114 and 116, for each of two bottles B1 and B2 held by the module. As is apparent, recesses 114 and 116 are disposed along an axis "l" of module 100, FIG. 4, which is the dimension that aligns with a radius of rotor 34, FIG. 1. Base 112, FIG. 3, is joined to sidewall 160 by any conventional means, e.g., by welding, by adhesive, by mechanical latches, etc.

Top member 130 comprises a generally flat plate 132 provided with raised bosses 134, and depending fingers 136 with snap latches 138 for locking under the rim of the access end 140 of a bottle B1 or B2. (Opposite ends 142 of the bottles are retained in recesses 114 and 116). Apertures 144 in bosses 134 are shaped to receive stoppers 146, such as duck-billed stoppers. A foil seal 148 is applied directly to the end 140 of the bottle, before it is inserted into latches 138. A side skirt 150 wraps around plate 132 and terminates in a portion, not shown, that extends down along and in contact with sidewall 160.

Figure 4:
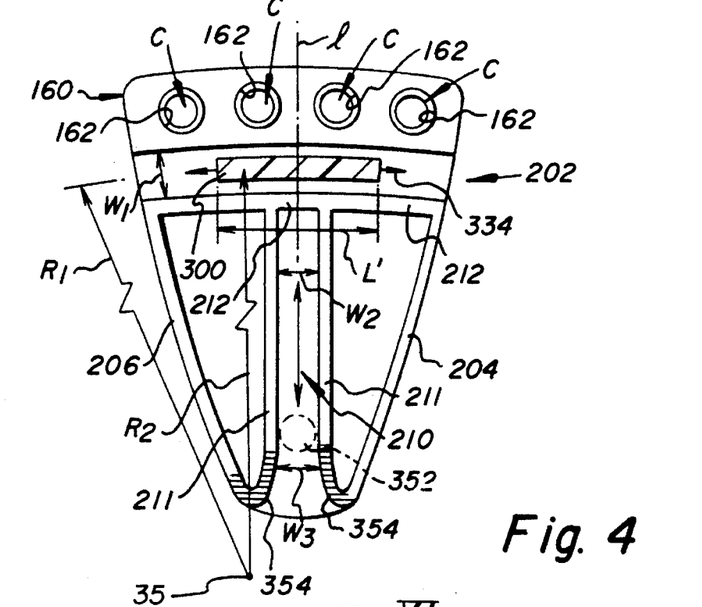
FIG. 4 is a bottom view of the undersurface of a module, taken generally along the line IV—IV of FIG. 3.

Sidewall 160 can have any desired shape and thickness, but preferably it has a plurality of, e.g., four cylindrical apertures 162, FIG. 4, extending the full height of the wall. A stack of reaction cuvettes, preferably shaped as cups or wells C, FIG. 2, is mounted within each aperture. The position of module 100 in place on rotor 34, FIG. 1, is such that the stacks of cuvettes are located over ring 52, for ready dispensing by mechanism 43, FIG. 2, at station 14.

Preferably, top member 130 interlocks with side wall 160 by reason of a tooth 190 snapping under a ledge 194 defining a groove 196. This prevents, once assembled, bottles B1 and B2 from being accidentally interchanged.

In accordance with one aspect of the invention, module 100 is provided with a surface, preferably an undersurface 200, FIG. 3, in which an arcuate groove 202 is formed, FIG. 4, of a length extending across the full width from side 204 to side 206. The arc of the groove has a predetermined radius $R_1$ and a width $W_1$. Preferably, a second, linear groove 210 is also formed within opposed sidewall 211 in surface 200, aligned with center axis "l", which in turn aligns with a radius of the rotor when the module is inserted onto the rotor. Hence groove 210 is generally perpendicular to groove 202. Most preferably, groove 210 does not connect with groove 202 because of barrier wall 212 that extends across groove 210 to separate it from groove 202, FIG. 3. However, the portion 212' of wall 212, FIG. 4, that actually closes off groove 210 could be eliminated, so long as tongue 300, described hereinafter, has a length L', as shown, which exceeds width $W_2$ groove 210.

To transfer module 100 into and out of the rotor, a transfer member is provided, which is preferably a tongue 300, FIG. 3, threadably mounted on a worm gear 302 so as to linearly advance or retreat therealong, arrow 304, pushing and pulling, respectively, groove 202 and hence module 100 onto and off of surface 310 of rotor 34. Tongue 300 is arcuate with a radius of curvature $R_2$ that is substantially equal to radius $R_1$ of groove 202, FIG. 4. Tongue 300 extends upwardly from a horizontal plate 312, FIGS. 5 and 6, which slides within a groove 314 provided by two fixed opposed rails 316, 318 at the module load station L, on which module 100 slideably rests, FIG. 7. (The position of plate 312 when advanced is shown in phantom in FIG. 7). Gear 302 is driven (rotated, arrow 325, FIG. 5) via a coupling 320 by any suitable motor 322, such as a stepper motor, FIG. 6. Rails 316 and 318 extend through a doorway 330 in enclosure wall 332, FIGS. 6 and 7, into a position A inside the enclosure of the rotor defined by the wall 332, and adjacent to rotor 34, FIG. 6. Gear 302 is journalled at bushing 334 located even further inside rotor wall 332, under rotor 34.

Figure 6:
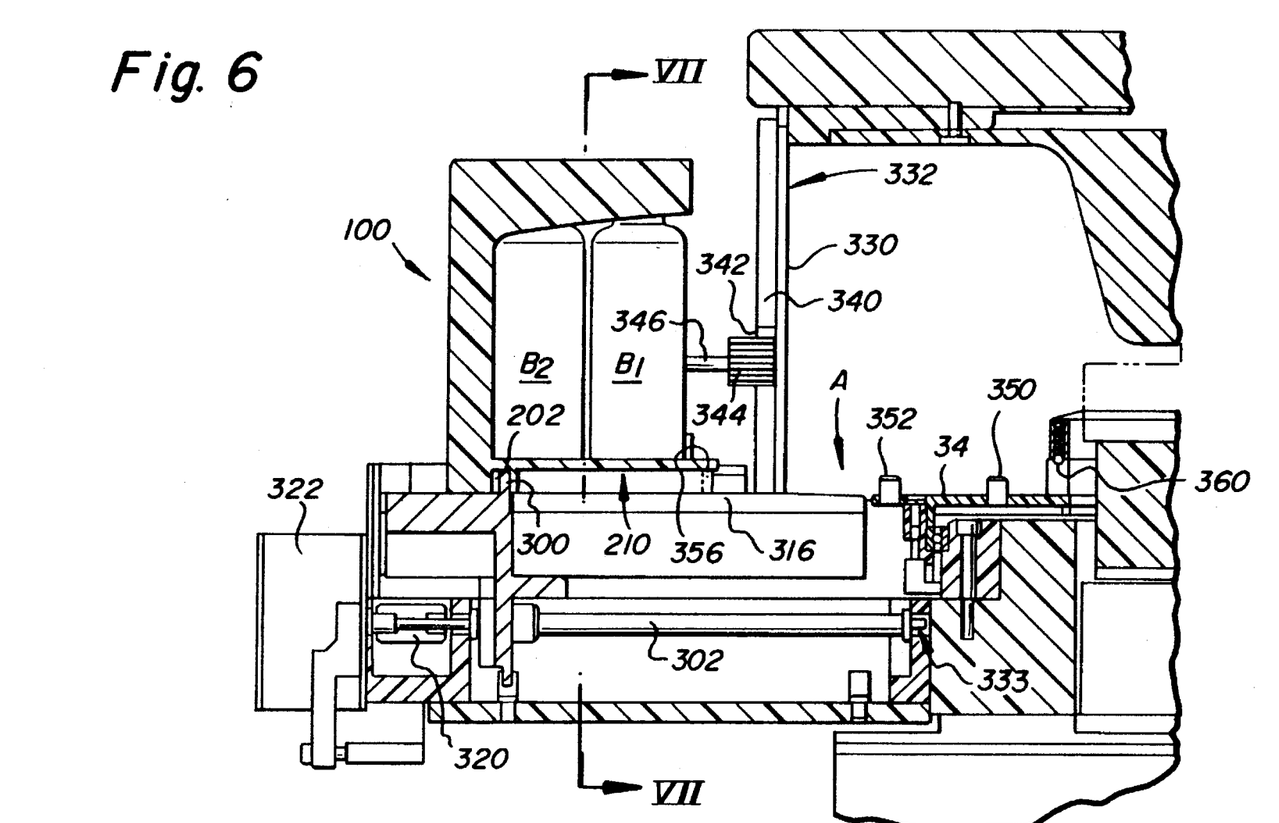
FIG. 6 is a fragmentary elevational view in section taken generally along the line VI—VI of FIG. 5 with the module in place.
Figure 7:
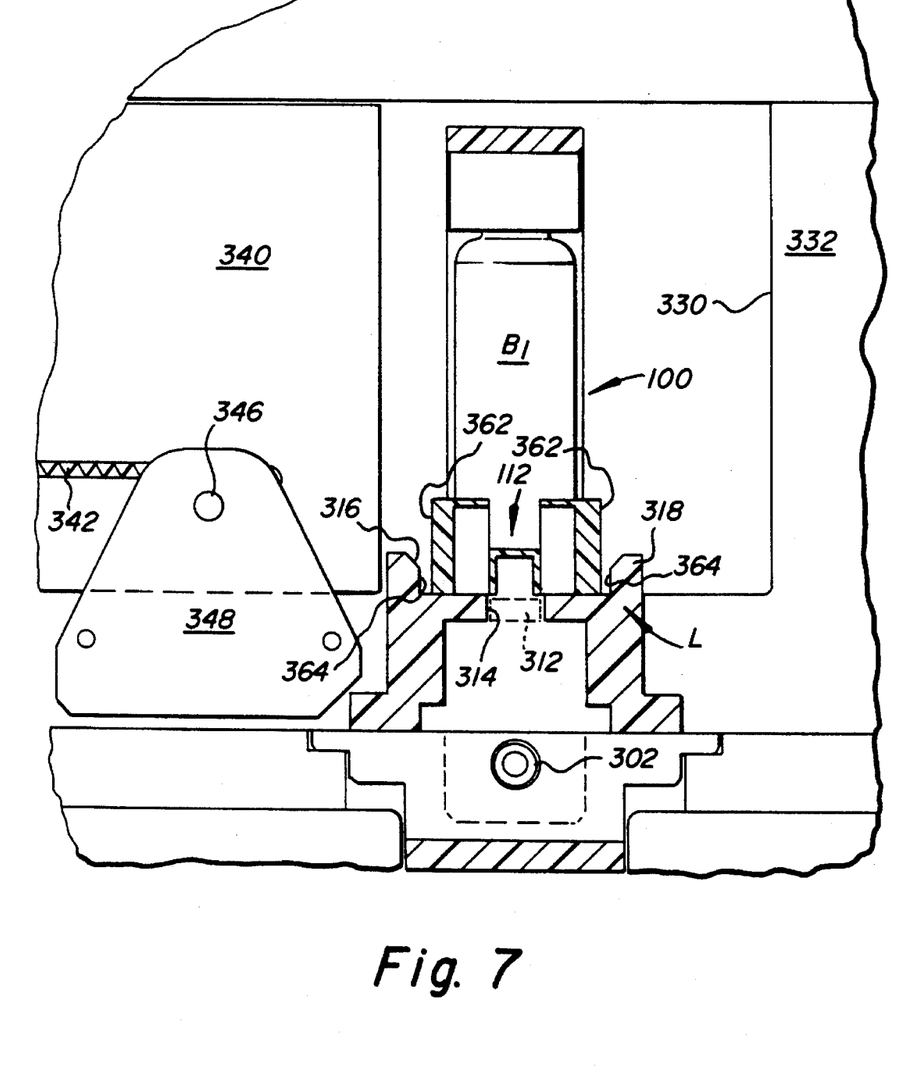
FIG. 7 is a section view taken generally along the line VII—VII of FIG. 6.

Doorway 330 is preferably opened and closed by a sliding door 340, FIG. 6, driven by a rack 342 on the door and a pinion 344 rotated on a shaft 346, as driven by a motor 348, FIG. 7.

To cooperate with and align module groove 210 with a radius of rotor 34, surface 310 of rotor 34, FIG. 3, preferably includes guides 350, 352 projecting upwardly, of a width dimension $W_3$, FIG. 4, which readily slides within groove 210 as module 100 is moved onto rotor 34. Because guides 350, 352 do the aligning, it is not necessary that the outer walls 362 of module 100, FIG. 7, fit snug against inside surfaces 364 of rails 316, 318. Walls 211 are preferably beveled outwardly at 354 to act to center guides 350, 352 within groove 210.

To temporarily lock a module 100 in place within enclosure wall 332 and on rotor 34, a releasable spring-biased ball detent 360 is provided at a location further within enclosure 332 than is guide 350, FIG. 6, to engage a mating opening 356 in base 112 of module 100. The spring of the detent has a spring constant that will allow the spring to collapse when a module starts to retreat off the rotor under the action of tongue 300, thus releasing the module.

The operation of the invention will be readily apparent from the preceding. Specifically, a module 100 is manually placed on the loading and unloading station L, FIG. 5, formed by rails 316, 318 and plate 312, so that tongue 300 is inserted into groove 202. At this juncture, the station L either automatically senses the presence of module 100, such as by the triggering of a limit switch on tongue 100, or the operator presses a "start" button.

In either case, the actual loading into the rotor waits until an empty receiving station on rotor 34 is available, aligned with load station L. Thus, the invention does not require attendance by the operator. When an empty station is positioned opposite station L. Door 340 is opened, and gear 302 rotates automatically so as to push tongue 300, groove 202 and module 100 into and through doorway 330, with module 100 continuing on in a direction, arrow 304, FIG. 5, that aligns guides 352 and 352 with groove 210, FIG. 6. Continued advance then mounts module 100 onto rotor 34, FIG. 3, with ball detent 360, FIG. 6, snapping into hole 356. When in this position, FIG. 3, tongue 300 can remain inside wall 332 of the rotor, because as the rotor rotates, arrow 334, FIG. 4, (with doorway 330 closed by door 340), grooves 202 of any modules mounted on rotor 34 easily slide over stationary tongue 300 since tongue 300 and grooves 202 have substantially the same arcuate radius of curvature. While inside enclosure wall 332 of the rotor, the contents of bottles $B_1$ or $B_2$ can be accessed through seals 148, and cuvettes C of the module can be dispensed. When any of the modules is spent and ready to be withdrawn, door 340 is opened, and tongue 300 pulls, arrow 304, groove 202 and hence module 100 out of the rotor and back into loading station L, FIG. 5, for manual unloading.

Figure 5:
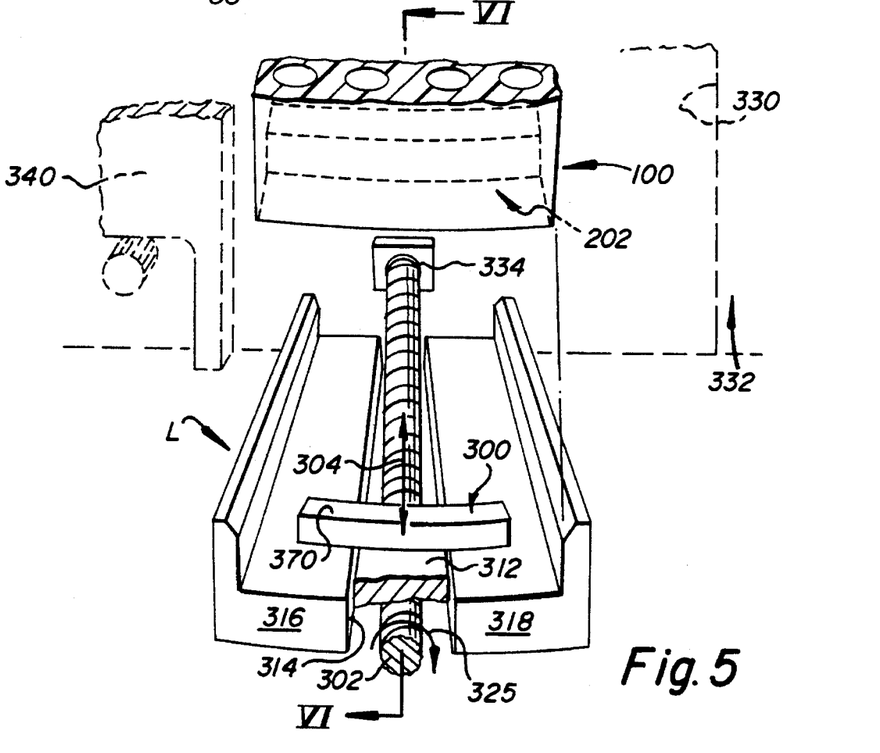
FIG. 5 is a fragmentary, exploded isometric view of a module's engagement with the transfer mechanism outside the enclosure of the rotor.

Optionally, not shown, a blinking light can be mounted on top surface 370 of tongue 300, FIG. 5, to inform the operator when in fact it is outside enclosure wall 332 and hence ready for a new module to be loaded onto it.

In this fashion, the same transfer mechanism of station L can be used to unload a module as is used to load a module.

Alternatively, FIG. 1, a separate unloading station U can be located spaced away from station L around the rotor periphery, for use with a separate tongue 300' whose function it is solely to unload, arrow 304' spent modules used and loaded from station L using tongue 300. In such a case, station U is preferably constructed identically to station L, including a door for the rotor doorway, not shown.

Figure 8:
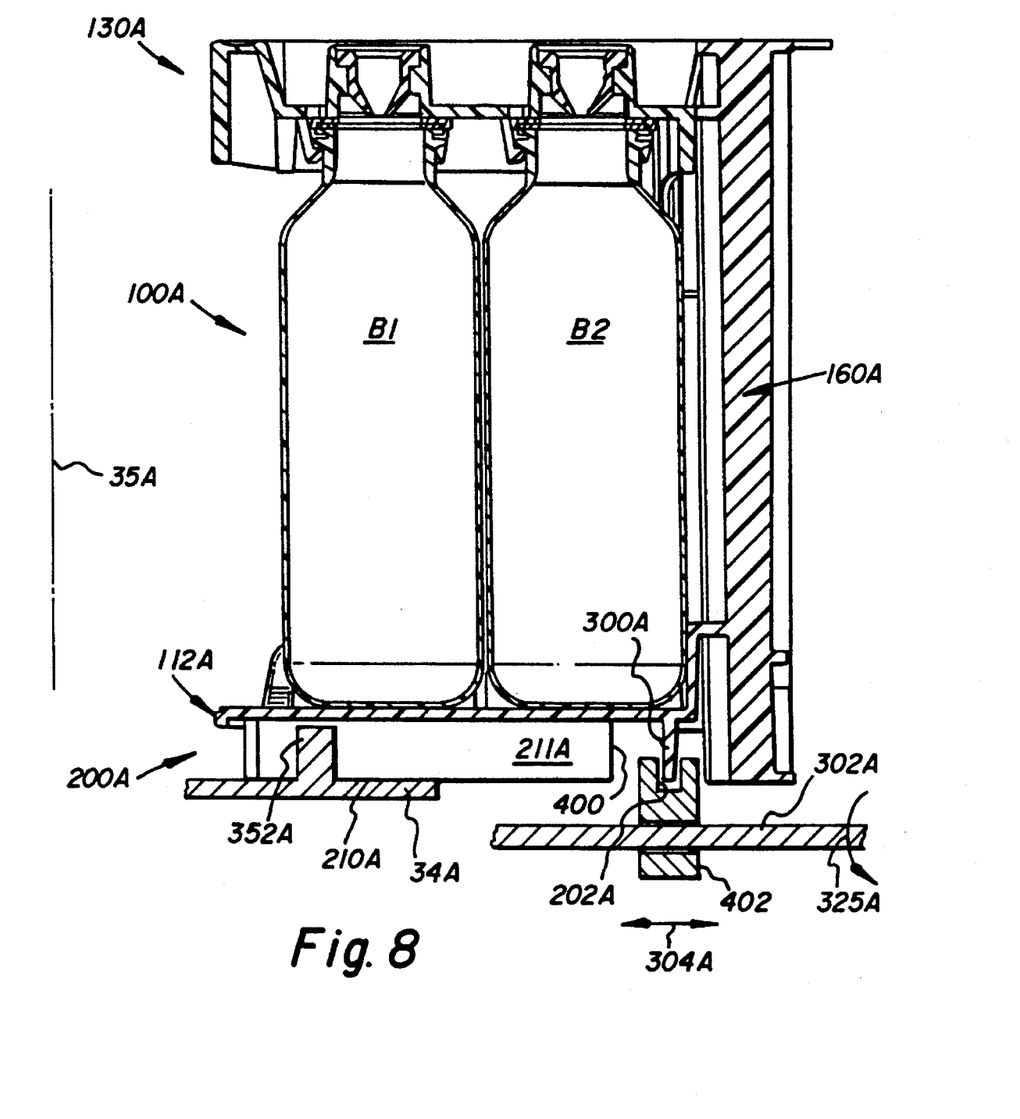
FIG. 8 is an elevational view in section similar to that of FIG. 3, except that it illustrates an alternative embodiment of the invention.

It will be readily apparent that it is not essential that the tongue be part of the transfer mechanism and the groove part of the module. Rather, they can be reversed, as shown in FIG. 8. Parts similar to those previously described bear the same reference numerals, to which the distinguishing suffix "A" has been appended. Thus, as before, module 100A is pushed and pulled onto rotor 34A via the cooperative aligning effect of guides such as 352A and linear groove 210A, the module mounting two bottles $B_1$, $B_2$, and reaction cuvettes (not shown) between the base 112A, top member 130A and sidewall 160A. The rest of the construction of module 100A is as described for the previous embodiment, except that on undersurface 200A, a tongue 300A is formed out of the wall closing off groove 210A, by notching out sidewalls 211A at portion 400. This in turn cooperates with a groove 202A formed in the transfer member 402 threaded onto worm gear 302A as before. As gear 302A rotates, arrow 325A, groove 202A pushes or pulls tongue 300A, arrow 304A, and hence module 100A into or out of the rotor. When fully inside the rotor, modules 100A can be rotated with member 402 retained inside, due to the free sliding of tongue 300A within groove 202A.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. In an analyzer comprising a source of reagents and reaction cuvettes, said analyzer including a rotor having a periphery and an axis of rotation, a drive for rotating said rotor about said axis, said source comprising a removable module containing a reagent container and a stack of said cuvettes, said rotor including receiving stations constructed to receive and engage said modules, a load and unload station for receiving and returning individual modules from and to an operator, and transfer means for transferring an individual module on said load station in a first direction onto said rotor, the improvement wherein said transfer means and said modules comprise between them, a member with a projecting tongue on said transfer means, and a first groove on a surface of said modules cooperatively shaped for reception of said tongue within it, said groove being dimensioned to freely slidably accommodate said tongue within it, said tongue and groove having an extension in a direction that is misaligned with said first direction, so that said tongue and groove are effective to move an engaged module onto or off of said rotor along said first direction, said groove being arcuately shaped to extend from one edge of each module to an opposite edge in a direction defining a portion of a circle that is concentric with the axis of said rotor when a module is inserted into the rotor, so that said tongue can be slid out of said groove in a given module by rotating the rotor while said tongue is still inside the periphery of said rotor; and a second groove in said module surface, extending at an angle to said first groove.

2. In an analyzer comprising a source of reagents and reaction cuvettes, said analyzer including a rotor having a periphery and an axis of rotation, a drive for rotating said rotor about said axis, said source comprising a removable module containing a reagent container and a stack of said cuvettes, receiving stations on said rotor constructed to receive and engage said modules, a load and unload station for receiving and returning individual modules from and to an operator, and transfer means for transferring an individual module on said station in a first direction onto said rotor;

the improvement wherein each of said modules includes a surface, a linear groove part-way along the surface of said modules, and an arcuate groove in said surface to which said linear groove extends generally perpendicularly, so that said linear groove can cooperate with guides projecting from said receiving stations to direct the insertion of said module onto a receiving station along a prescribed path, and said arcuate groove can cooperate with an engaged tongue of said transfer means as a module is forced to rotate by one of said stations over said tongue.

3. An analyzer as defined in claim 2, wherein said arcuate groove and said linear groove are separated from each other by a wall.

4. An analyzer as defined in claim 2, and further including releasable biasing means for releasably engaging said modules when they are fully inserted into said rotor, said biasing means including a spring having a constant effective to hold a module in position except when said transfer means withdraws a module from said rotor.

5. An analyzer as defined in claim 2, wherein said transfer means comprises said tongue, and further including a drive constructed to reciprocate said tongue in said first direction, and guides projecting upwardly from each of said receiving stations to receive a module along a path extending generally on a radius of said rotor.

6. In an analyzer for processing modules of reaction cuvettes, said analyzer including at least one of said modules, a rotor for holding said modules at stations so that said modules are generally aligned with a rotor radius, a drive for said rotor, transfer means for pushing one of the modules onto one of said stations on said rotor, and a drive for reciprocating said transfer means towards and away from said rotor along a linear path;

the improvement wherein one of a group consisting of said modules and said transfer means include a projecting tongue and the other of said group of said modules and said transfer means includes an arcuate groove, said groove and said tongue being cooperatively shaped such that when relative pushing or pulling movement is provided between said tongue and said groove, one against the other, the module is pushed or pulled, respectively, relative to said rotor, and when said tongue is freely slid within said rotor, all of said modules can be rotated without withdrawing said tongue or groove from the vicinity of said rotor, and further including releasable biasing means for releasably engaging said modules when they are fully inserted into said rotor, said biasing means including a spring have a spring constant effective to hold a module in position except when said transfer means withdraws a module from said rotor.

* * * * *